(12) United States Patent
Uetake et al.

(10) Patent No.: US 9,422,100 B2
(45) Date of Patent: Aug. 23, 2016

(54) FILTERING DISCHARGE CONTAINER

(75) Inventors: Yorihisa Uetake, Aichi (JP); Hirokazu Mihashi, Osaka (JP); Seiji Yoshimura, Osaka (JP)

(73) Assignees: Taisei Kako Co., Ltd., Osaka (JP); Nihon Tengantaku Kenkyusyo Co., Ltd., Aichi (JP)

( * ) Notice: Subject to any disclaimer, the term of this patent is extended or adjusted under 35 U.S.C. 154(b) by 22 days.

(21) Appl. No.: 14/398,010

(22) PCT Filed: May 9, 2012

(86) PCT No.: PCT/JP2012/061846
§ 371 (c)(1),
(2), (4) Date: Oct. 30, 2014

(87) PCT Pub. No.: WO2013/168243
PCT Pub. Date: Nov. 14, 2013

(65) Prior Publication Data
US 2015/0122845 A1     May 7, 2015

(51) Int. Cl.
*A61F 9/00*     (2006.01)
*A61J 1/14*     (2006.01)
(Continued)

(52) U.S. Cl.
CPC .......... *B65D 83/0094* (2013.01); *A61F 9/0008* (2013.01); *A61J 1/1443* (2013.01); *B65D 47/18* (2013.01); *B65D 47/2075* (2013.01); *B65D 47/2093* (2013.01); *B65D 51/1616* (2013.01); *B65D 83/0055* (2013.01)

(58) Field of Classification Search
CPC .......... B65D 83/0055; B65D 83/0094; B65D 47/18; B65D 47/2075; B65D 47/2093; B65D 51/1616; A61F 9/0008; A61J 1/1443
See application file for complete search history.

(56) References Cited

U.S. PATENT DOCUMENTS 6,672,479 B2 *   1/2004   Shiraishi ................ B65D 23/02
                                                              222/105
6,708,850 B2 *   3/2004   Uetake .................. A61F 9/0008
                                                              222/105

(Continued)

FOREIGN PATENT DOCUMENTS

JP     2002263166 A     9/2002
JP     2005160972 A     6/2005

(Continued)

OTHER PUBLICATIONS

International Search Report dated Jul. 10, 2012.

*Primary Examiner* — Frederick C Nicolas
(74) *Attorney, Agent, or Firm* — Wood, Phillips, Katz, Clark & Mortimer

(57) ABSTRACT

A filtering discharge container employing a delaminatable bottle was provided, which reliably prevents a content liquid from leaking out before the first use, and reduces a discharging resistance during the second and subsequent use. An engagement portion (31*c*) is provided in an outlet passage of a mouth cap (3). A plug (34) is engaged with the engagement portion (31*c*) in such a manner that the plug (34) can be disengaged from the engagement portion (31*c*) by an internal pressure of an inner layer bag (22) increased by squeeze-deforming a body of an outer layer bottle (21). The outlet passage is closed with the plug (34) engaged with the engagement portion (31*c*). After the plug (34) is disengaged from the engagement portion (31*c*), liquid communication is established between the inside of the inner layer bag (22) and a filter (33).

3 Claims, 6 Drawing Sheets

(51) Int. Cl.
*B65D 83/00* (2006.01)
*B65D 47/18* (2006.01)
*B65D 51/16* (2006.01)
*B65D 47/20* (2006.01)

(56) References Cited

U.S. PATENT DOCUMENTS

| | | | |
|---|---|---|---|
| 7,971,753 B2 * | 7/2011 | Mihashi | A61F 9/0008 222/105 |
| 2002/0153386 A1 * | 10/2002 | Uetake | A61F 9/0008 222/1 |
| 2003/0230596 A1 | 12/2003 | Masuda | |
| 2006/0054635 A1 * | 3/2006 | Iwahashi | A61F 9/0008 222/107 |
| 2011/0144598 A1 * | 6/2011 | Mihashi | A61F 9/0008 604/295 |

FOREIGN PATENT DOCUMENTS

| | | |
|---|---|---|
| WO | 0222458 A1 | 3/2002 |
| WO | 0238464 A1 | 5/2002 |
| WO | 2005118152 A1 | 12/2005 |
| WO | 2009147952 A1 | 12/2009 |
| WO | 2010013131 A1 | 12/2010 |

* cited by examiner (a)

(b)

FILTERING DISCHARGE CONTAINER

TECHNICAL FIELD

The present invention relates to a filtering discharge container.

BACKGROUND ART

The applicants of the present invention disclose prior-art filtering discharge containers each employing a delaminatable bottle (delaminatable laminate bottle) to be advantageously used for aseptic eyedropper containers, for example, in the following PLT1 and PLT2.

CITATION LIST

Patient Literature

PLT1: JP-2002-80055-A
PLT2: JP-2009-179403-A

These prior-art filtering discharge containers each include an outer layer bottle having a squeeze-deformable body and a mouth portion provided at an upper end of the body, an inner layer bag provided in the outer layer bottle and having an opening connected to the mouth portion of the outer layer bottle, and a mouth cap attached to the mouth portion of the outer layer bottle. The outer layer bottle has an inlet hole through which outer air is introduced between the outer layer bottle and the inner layer bag. The mouth cap has an outlet passage through which a content liquid contained in the inner layer bag is discharged from the inner layer bag, and a filter and a check valve are provided in the outlet passage.

The filter is a membrane filter or the like which has a multiplicity of minute pores and prevents passage of virus and bacteria. In PLT1, the check valve principally includes a valve body resiliently supported by a thin piece. In PLT2, the check valve principally includes a valve body made of a resilient material and having a cross-shaped orifice formed in a valve head of the valve body.

SUMMARY OF INVENTION

Technical Problem

The multiplicity of minute pores of the filter are closed with water in a so-called air-locked state when being wetted. In this state, air cannot pass through the filter, unless a pressure higher than a bubble point of the filter is applied to the filter. Therefore, the filter is maintained in a dry state during the storage of the container before the first use.

However, a highly osmotic medicinal liquid is liable to leak from the check valve of the prior-art check valve mechanism to wet the filter, which is in turn air-locked. Therefore, air remaining on the upstream side of the filter after the first use problematically prevents the discharge of the content liquid. In the check valve disclosed in PLT1, a valve hole is closed with a disk-shaped valve body in abutment against the valve hole. Therefore, a relatively small contact force is present between the valve body and the valve hole, so that the highly osmotic medicinal liquid is likely to leak from between the valve body and the valve hole. In the check valve disclosed in PLT2, the orifice is defined by an incision, and no external force acts on the orifice to firmly close the orifice, so that the highly osmotic medicinal liquid is likely to leak from the orifice.

In the check valve mechanism, the valve body is provided for drawing the medicinal liquid from the downstream side of the filter. When the content liquid is dispensed dropwise in the second and subsequent use, it is necessary to lift the valve head to open the orifice. Therefore, the outer layer bottle should be relatively heavily squeeze-deformed against the lifting resistance to dispense the content liquid dropwise. This makes it impossible to provide a comfortable use feeling.

It is therefore an object of the present invention to provide a filtering discharge container employing a delaminatable bottle, which reliably prevents the content liquid from leaking to the filter before the first use, and has a reduced discharging resistance during the second and subsequent use.

Solution to Problem

To achieve the object described above, the present invention has the following technical aspects:

According to the present invention, there is provided a filtering container, which includes: an outer layer bottle including a squeeze-deformable body and a mouth portion provided at an upper end of the body; an inner layer bag provided in the outer layer bottle and having an opening connected to the mouth portion of the outer layer bottle; and a mouth cap attached to the mouth portion of the outer layer bottle. The outer layer bottle has an inlet hole through which outer air is introduced between the outer layer bottle and the inner layer bag. The mouth cap has an outlet passage through which a content liquid contained in the inner layer bag is discharged from the inner layer bag, and a filter is provided in the outlet passage. The filtering container further includes: an engagement portion provided on an upstream side of the filter in the outlet passage of the mouth cap; and a plug engaged with the engagement portion in such a manner that the plug can be disengaged from the engagement portion by an internal pressure of the inner layer bag increased by squeeze-deforming the body of the outer layer bottle. The outlet passage is closed with the plug engaged with the engagement portion. After the plug is disengaged from the engagement portion, liquid communication is established between the inside of the inner layer bag and the filter. In the present invention, the term "discharge" means that the content liquid is dispensed dropwise from a distal nozzle portion, that a predetermined amount of the content liquid is caused to flow out in the form of continuous stream, and the like.

In the filtering discharge container according to the present invention, when the plug is engaged with the engagement portion, a space defined between the filter and the engagement portion is filled with air, and the outlet passage is reliably closed with the plug engaged with the engagement portion. This prevents the content liquid contained in the inner layer bag from leaking from between the outlet passage and the plug. In the prior-art check valve mechanism described above, it is necessary to restore the check valve into an outlet passage closed state. With a limitation in the closing force of the closed orifice, therefore, it is impossible to firmly close the orifice. In the present invention, once the plug is disengaged from the engagement portion, the plug is simply required to be supported in the disengaged state. Therefore, the filtering container can be designed in primary consideration of the closing force required for closing the outlet passage in the engagement state. Even if a highly osmotic medicinal liquid is contained as the content liquid in the container, the leakage of the content liquid can be reliably prevented. Although the filtering container is configured such that the plug is engaged with the engagement portion, the plug can be disengaged from the engagement portion by an internal pressure of the inner layer bag increased by squeeze-deforming the body of the outer layer bottle with the inlet hole being closed. This obviates the need for performing a special unplugging operation when the content liquid is discharged for the first time, but the outer layer bottle is simply required to be relatively heavily squeeze-deformed only in the first discharging operation. When the plug is disengaged from the engagement portion, the plug is liable to be instantaneously popped out from the engagement portion by the internal pressure of the pressurized inner layer bag. This results in plosive vibrations. Even if the state of the plug cannot be visually checked from the outside, the user can recognize the communication of the outlet passage based on the vibrations. When the plug is disengaged from the engagement portion in the first discharging operation, the air present between the filter and the engagement portion is expelled from the filter to the outside by the content liquid flowing toward the filter from the periphery of the plug, and then the space defined between the filter and the engagement portion is filled with the content liquid. Therefore, the wetted filter prevents outer air from being drawn from the downstream side of the filter to the upstream side of the filter. In the second and subsequent discharging operation, therefore, the content liquid can be smoothly dispensed dropwise by a relatively small squeeze force. As the amount of the content liquid decreases, the inner layer bag is deformed to be shrunk. The outer layer bottle is thereafter squeeze-deformed with the inlet hole being closed. Thus, the air introduced between the outer layer bottle and the inner layer bag is compressed to apply a compressive force to the inner layer bag via the compressed air. When the plug is disengaged from the engagement portion, the air present in the space defined between the filter and the plug is expelled to be replaced with the content liquid in the space. At this time, bubbles are liable to occur in the content liquid. However, only the content liquid passes through the wetted filter to be discharged. Thus, the content liquid flowing downstream of the filter contains no bubble. The content liquid can be stably dispensed dropwise in a predetermined amount without variations in dispensing amount and occurrence of bubble splash at a nozzle tip.

The filtering discharge container according to the present invention may further include a resilient support member which urges the plug away from the engagement portion. This arrangement makes it possible to increase an engagement force between the plug and the engagement portion and to reduce a squeeze force required to be applied to the outer layer bottle for disengaging the plug from the engagement portion in the first discharging operation, thereby more reliably preventing the leakage of the content liquid and further improving the use feeling.

The filtering discharge container may be configured such that the plug is supported in a disengaged position by the resilient support member after the plug is disengaged from the engagement portion, or may further include a support portion which supports the plug in the disengaged position after the plug is disengaged from the engagement portion. Thus, the resilient support member or the support portion supports the disengaged plug in the disengaged position, thereby preventing the plug from being re-engaged with the engagement portion. Therefore, only a small squeeze force is required for the second and subsequent discharging operation.

The resilient support member is preferably molded integrally with the plug. This reduces the number of the components, simplifies the construction, and facilitates the assembling.

The inner layer bag preferably has restorability for sucking the content liquid back to the upstream side of the filter from the downstream side of the filter in the outlet passage after the content liquid is discharged. With this arrangement, the inner layer bag shrunk due to the decrease in the amount of the content liquid is slightly expanded to be restored after the first discharging operation, whereby the content liquid remaining on the downstream side of the filter in the outlet passage is sucked back to the upstream side of the filter. This prevents the content liquid from being exposed to the outer air, thereby preventing proliferation of bacteria on the downstream side of the filter. Further, the air present between the filter and the plug is expelled to the outside to be replaced with the content liquid in the first discharging operation, so that the volume of the inner layer bag is significantly reduced due to the squeeze-deformation of the container body in the first discharging operation. Therefore, the inner layer bag is likely to have a sufficient resilient restoration force even with several droplets of the content liquid discharged in the first discharging operation. Thus, the remaining liquid can be sufficiently sucked back from the downstream side of the filter by the inner layer bag even in the first content liquid discharging operation. The restorability of the inner layer bag may be provided by the restoration resilience of the inner layer bag itself or may be provided by a force applied by the weight of the content liquid present in the inner layer bag to expand the inner layer bag.

The mouth cap includes: a plug holder having the engagement portion which is provided in an upwardly open state so as to be combined with the plug from above; a cover having a top portion; the filter which is provided on a lower side of the top portion of the cover; and the plug. The cover is fitted around the plug holder combined with the plug from above. This arrangement facilitates the plug combining operation, and makes it possible to reliably engage the plug with the engagement portion by pressing the plug against the engagement portion from above. The plug holder and the cover combined together can be handled as a single attachment component. Therefore, the mouth cap (attachment component) can be attached to the bottle mouth after a content liquid filling operation is performed in a content liquid filling plant. This improves the mass productivity and the quality control. The outlet passage extends through the plug holder and the cover, and an outlet nozzle portion provided at the top portion of the cover defines a part of the outlet passage downstream of the filter.

DESCRIPTION OF EMBODIMENTS

Preferred embodiments of the present invention will hereinafter be described with reference to the drawings.

Figure 1:
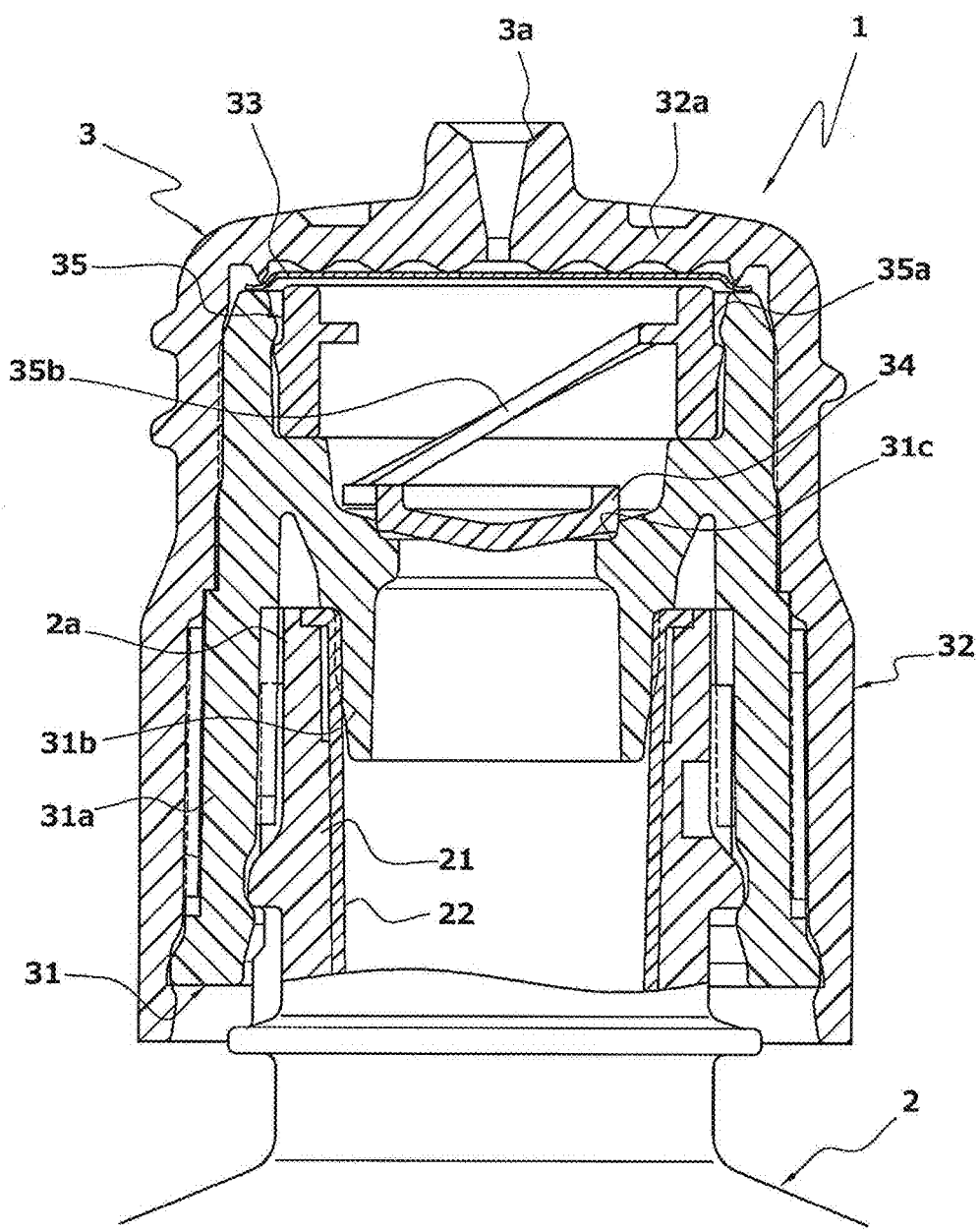
FIG. 1 is a sectional view showing a major portion of a filtering discharge container according to a first embodiment of the present invention in a sealed state.
Figure 2:
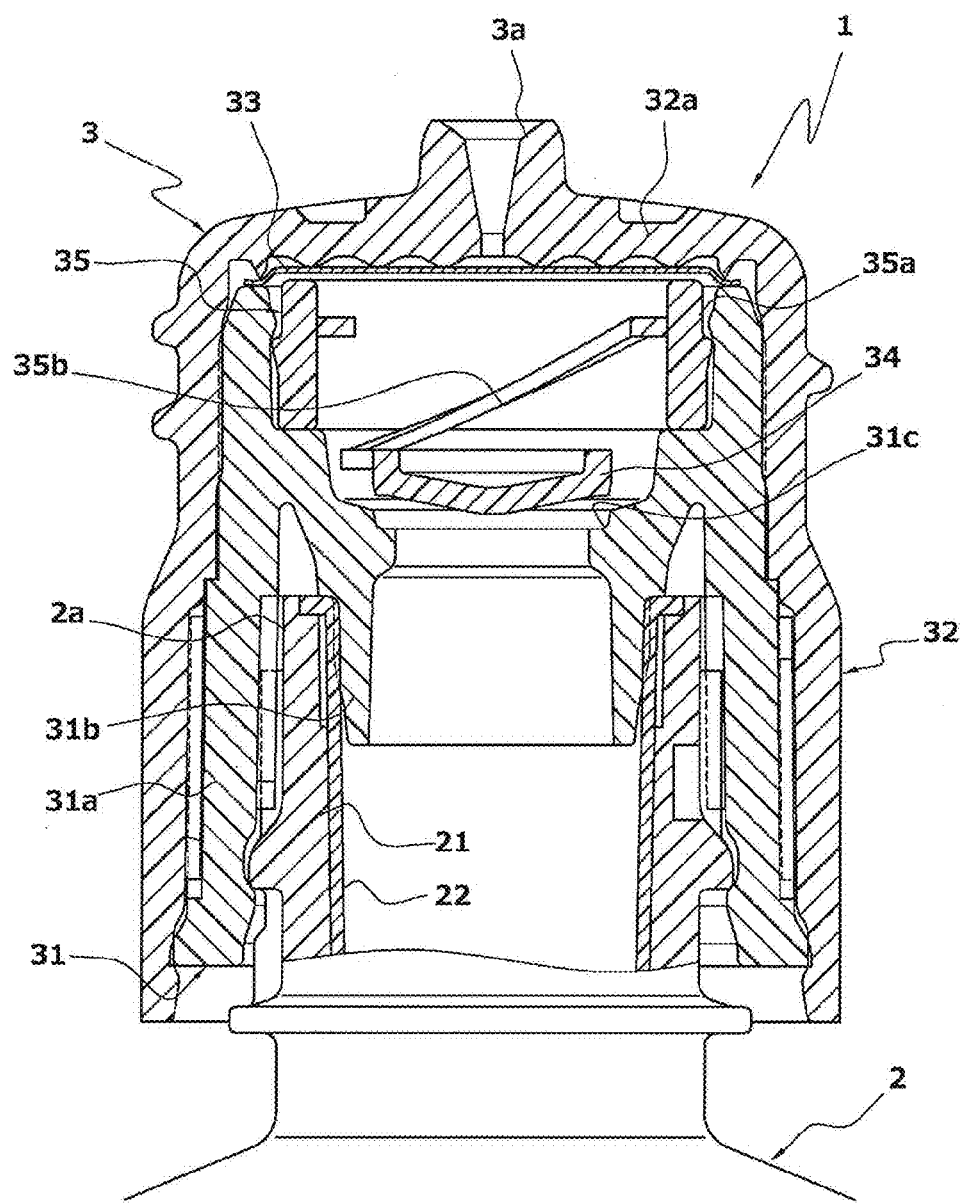
FIG. 2 is a sectional view showing the major portion of the container in an unsealed state.

FIGS. 1 and 2 illustrate an eyedropper container 1 as a discharge container including a delaminatable bottle according to a first embodiment of the present invention. The eyedropper container 1 has the same basic construction as disclosed in PLT1 and PLT2. The eyedropper container 1 includes a laminate bottle 2 having a double layer structure including an inner layer and an outer layer produced by blow-molding a bottomed tubular laminate parison, and a mouth cap 3 attached to a mouth portion 2*a* of the bottle 2. The mouth cap 3 has an outlet passage through which a content medicinal liquid is discharged. A filter 33 and a plug 34 for closing the outlet passage on an upstream side of the filter 33 with respect to a discharging direction until the first discharging operation are provided in the outlet passage of the mouth cap 3. The content medicinal liquid (fluid) contained in the bottle 2 flows through the outlet passage in the mouth cap 3 to be dispensed dropwise from a distal nozzle portion 3*a* by inverting the laminate bottle 2 and press-squeezing the body of the laminate bottle 2.

The laminate bottle 2 has a layered structure including an outer layer bottle 21 (squeeze bottle) defining the outer layer and an inner layer bag 22 (fluid containing bag) defining the inner layer. The outer layer bottle 21 and the inner layer bag 22 each have a hollow cylindrical mouth portion and a body having an oval cross section immediately after the blow molding. The outer layer bottle 21 is formed from a synthetic resin such as PET or SBS, and the inner layer bag 22 is formed from a synthetic resin (e.g., a polyolefin such as a polypropylene or a polyethylene) easily delaminatable from the outer layer bottle 21 and preferably withstanding electron beam sterilization and γ-ray sterilization. The mouth portion of the bag 22 serves as an opening through which the content medicinal liquid is discharged, and the opening of the bag 22 is fixedly connected to the mouth portion of the outer layer bottle 21.

The outer layer bottle 21 is configured such that an upper edge of a resiliently squeeze-deformable bottomed tubular body thereof is connected to the hollow cylindrical mouth portion via a shoulder having a diameter progressively reduced in an upward direction. The outer layer bottle 21 may have any configuration, and may have rigid front and back walls as disclosed in PLT2. The outer layer bottle 21 has an inlet hole (not shown) through which outer air is introduced between the outer layer bottle 21 and the inner layer bag 22. The inlet hole is preferably provided in the body of the outer layer bottle 21 as disclosed in PLT2, but may be provided in the bottom or the mouth portion of the bottle.

The body of the inner layer bag 22 has a film shape, and is easily deformable to be shrunk as the amount of the content medicinal liquid decreases. Further, the inner layer bag 22 has restoration resilience such that the content medicinal liquid remaining in the distal nozzle portion 3*a* of the outlet passage on a downstream side of the filter 33 with respect to the discharging direction after the discharge of the content medicinal liquid can be sucked back to the upstream side of the filter 33. On the other hand, the mouth portion of the inner layer bag 22 has a greater thickness than the body of the inner layer bag 22.

The mouth cap 3 includes a hollow cylindrical plug holder 31, a cover 32 fitted around the plug holder 31, and the filter 33 and the plug 34 described above. The outlet passage for the content medicinal liquid extends vertically through a center portion of the plug holder 31. The cover 32 has a disk-shaped top portion 32*a* (top plate), and the nozzle portion 3*a* extends vertically through the center of the top portion. The outlet passage through which the content medicinal liquid contained in the inner layer bag 22 is discharged is defined by the nozzle portion 3*a* and the center outlet passage of the plug holder 31. The top portion may entirely have a nozzle shape.

The plug holder 31 includes a tubular base portion 31*a* fitted around the mouth portion of the outer layer bottle 21, and a tubular content liquid outlet portion 31*b* provided integrally in the base portion 31*a* and having a smaller diameter than the base portion 31*a*. The content liquid outlet portion 31*b* is liquid-tightly fitted in the bottle mouth portion 2*a*. The content liquid outlet portion 31*b* has a plug engagement recess 31*c* (engagement portion) provided along an upper edge thereof as opening upward. An inner peripheral surface of the plug holder 31 has a diameter that is increased progressively or stepwise in an upward direction from the engagement portion 31*c*. A resilient support member 35 of the plug 34 is accommodated in an attachment recess (inner space) provided along an upper edge (downstream edge) of the plug holder 31.

The cover 32 is fitted around the plug holder 31 from above to be thereby combined with the plug holder 31. Before the combining, the filter 33 is provided on the lower side of the top portion 32*a*. The distal nozzle portion 3*a* of the mouth cap 3 is disposed at the center of the cover 32. The content medicinal liquid passing through the filter 33 is discharged from the distal nozzle portion 3*a* to the outside.

Usable as the filter 33 are a membrane filter, a sintered filter, a hydrophilic porous planar filter, a hydrophobic porous planar filter and the like which can prevent pathogenic bacteria and virus from passing through the filter 33 from the downstream side of the filter 33 (the outside of the container) to the upstream side of the filter 33 (the inside of the container) with respect to the discharging direction. The filter 33 is disposed on a downstream side of the plug 34 with respect to the discharging direction, and the outer peripheral edge of the filter is melt-bonded to the upper edge of the plug holder 31.

The plug 34 has a disk shape having a center portion slightly bulged downward, and is liquid-tightly engaged with the engagement portion 31*c*. In this embodiment, the plug 34 is squeezed into the engagement portion 31*c* from above, whereby an engagement force sufficient to prevent the plug 34 from being disengaged from the engagement portion 31*c* due to a slight increase in the internal pressure of the bottle or vibrations occurring during the storage or transportation of the bottle is generated between the plug 34 and the engagement portion 31*c*. In this embodiment, the plug 34 and the resilient support member 35 which supports the plug 34 are integrally molded to serve as a single plug member. The resilient support member 35 urges the plug 34 engaged with the engagement portion 31 upward (away from the engagement portion 31*c*) and, after the plug 34 is disengaged upward from the engagement portion 31*c*, supports the plug 34 in a disengaged position, supports the plug 34 in a position upwardly apart from the engagement portion 31*c*. An urging force to be applied by the support member 35 is smaller than the engagement force.

Figure 3:
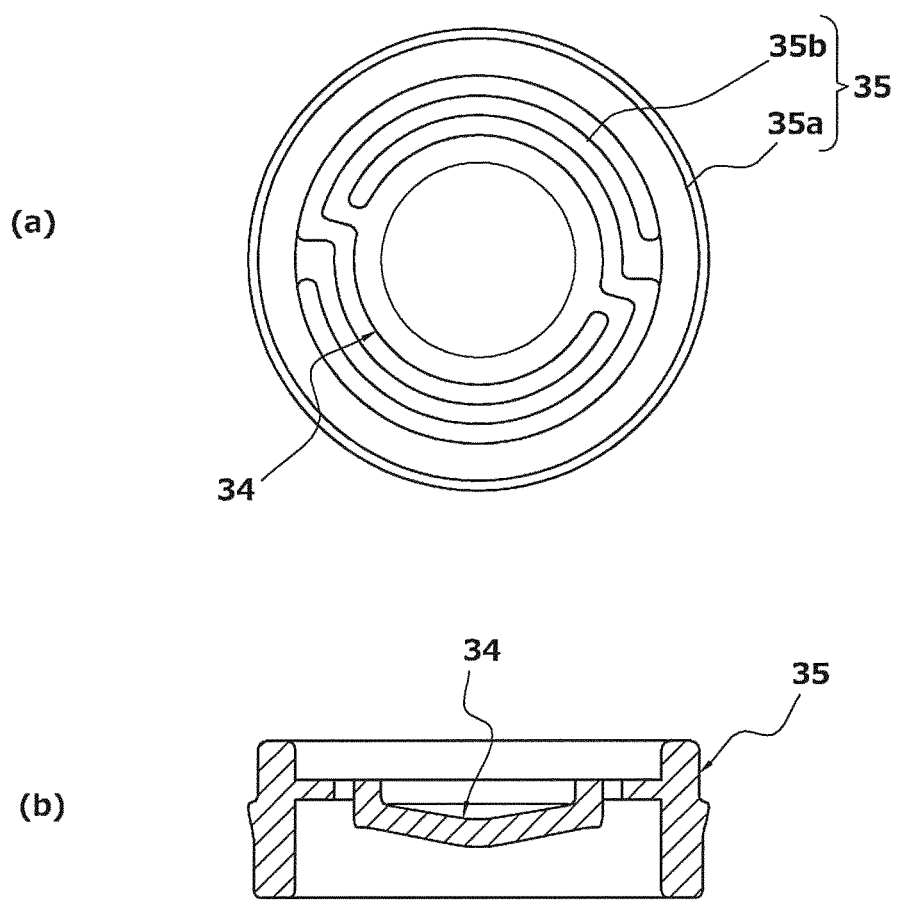
FIGS. 3(a) and 3(b) are a plan view and a vertical sectional view, respectively, showing a plug of the container.

More specifically, as shown in FIG. 3, the plug member including the resilient support member 35 and the plug 34 is an elastic member molded from a polyethylene, a polypropylene or an elastomer with the use of a methalocene catalyst. The resilient support member 35 includes a hollow cylindrical base portion 35*a* and a pair of arcuate resilient connection portions 35*b* which are integrally molded. The base portion 35*a* is fitted in an inner space defined in an upper edge portion of the plug holder 31, and the resilient connection portions 35*b* are provided on front and rear sides to connect the base portion 35*a* to the plug 34. The outer diameter of the plug 34 is smaller than the inner diameter of the base portion 35*a*, so that the content medicinal liquid uniformly flowing out from around the plug 34 disengaged from the engagement portion 31c flows through an inner peripheral portion of the base portion 35a toward the filter 33. The resilient support member 35 may be a member separate from the plug 34 and may be, for example, a spring. The number of the resilient connection portions 35b is not particularly limited. The number or the strength of the resilient connection portions 35b may be such that the plug 34 can be maintained in the position apart from the engagement portion 31c.

In the eyedropper container 1 according to this embodiment, the plug 34 is engaged with the engagement portion 31c as shown in FIG. 1 before the first discharging operation, whereby the outlet passage in the mouth cap 3 is reliably closed. Even if the content medicinal liquid is highly osmotic, the content medicinal liquid can be reliably prevented from leaking from the plug 34 to the downstream side. This prevents the air-lock which may otherwise occur when the filter 33 is wetted.

In the first discharging operation, the container 1 is inverted, and then the bottle body is squeeze-deformed with the inlet hole being closed with a finger. Thus, the internal pressure of the inner layer bag 22 is increased, whereby the plug 34 is pushed up from the engagement portion 31c by the internal pressure as shown in FIG. 2. At this time, the push-up force of the plug 34 is enhanced by the resilient connection portions 35b, so that the first discharging operation can be smoothly performed. In the first discharging operation, the air present between the filter 33 and the plug 34 is expelled through the dry filter 33 by the content liquid. Thereafter, the space under the filter 33 is filled with the content medicinal liquid. Thus, the filter 33 is constantly wetted with the content medicinal liquid.

In the second and subsequent discharging operation, the inside of the inner layer bag 22 constantly communicates with the filter 33, so that the squeeze force to be applied to the bottle body for the discharging is reduced. Thus, the discharging operation can be smoothly performed. Since the outer air cannot pass through the wetted filter, there is no possibility that the outer air is introduced to the upstream side of the filter in the second and subsequent discharging operation. This prevents a discharging failure which may otherwise occur due to the air lock. Further, the medicinal liquid remaining on the downstream side of the filter 33, i.e., the medicinal liquid remaining in the outlet nozzle portion 3a, is sucked back to the upstream side of the filter 33 by the restorability of the inner layer bag 22, thereby preventing the proliferation of bacteria in the nozzle portion 3a.

Figure 4:
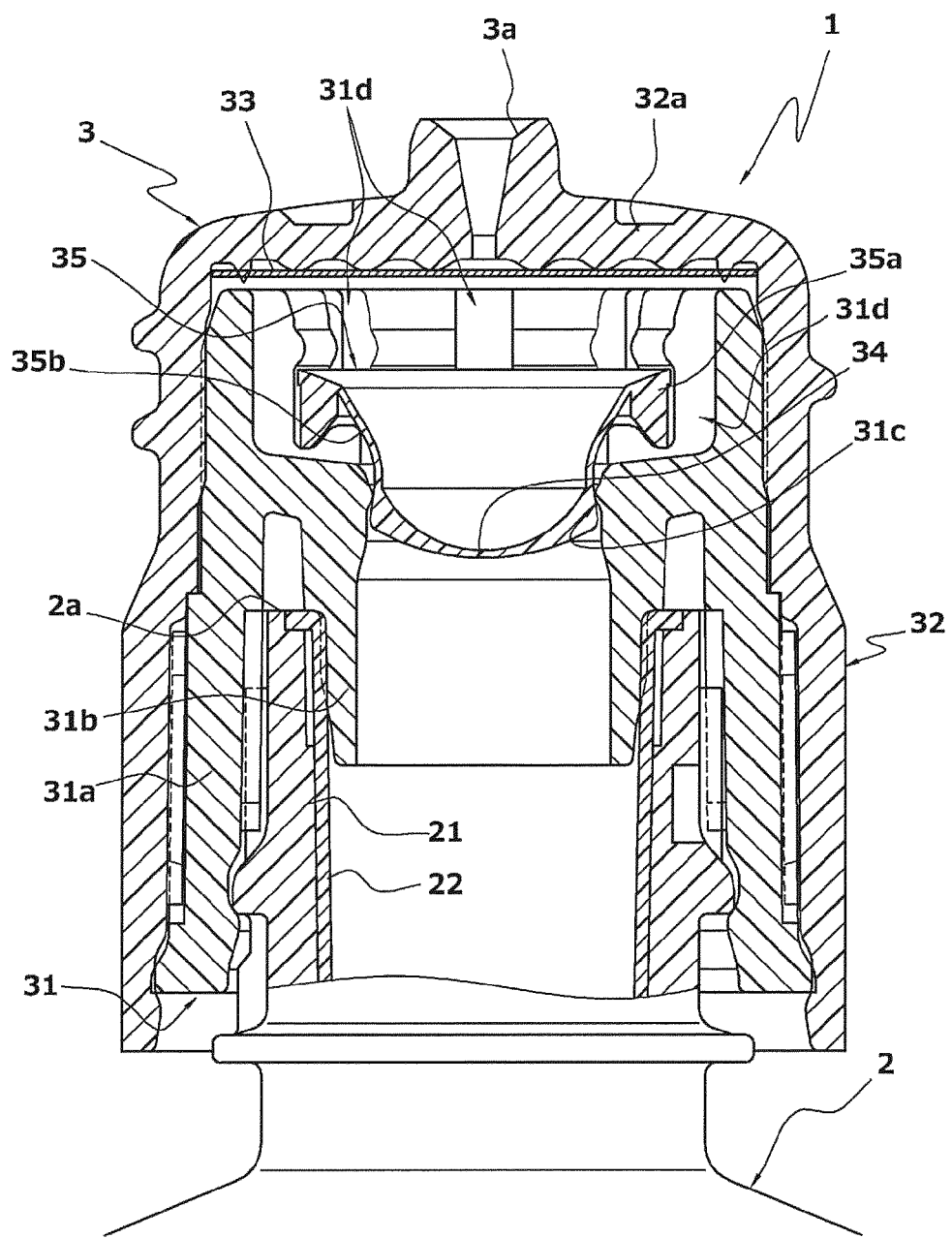
FIG. 4 is a sectional view showing a major portion of a filtering discharge container according to a second embodiment of the present invention in a sealed state.
Figure 5:
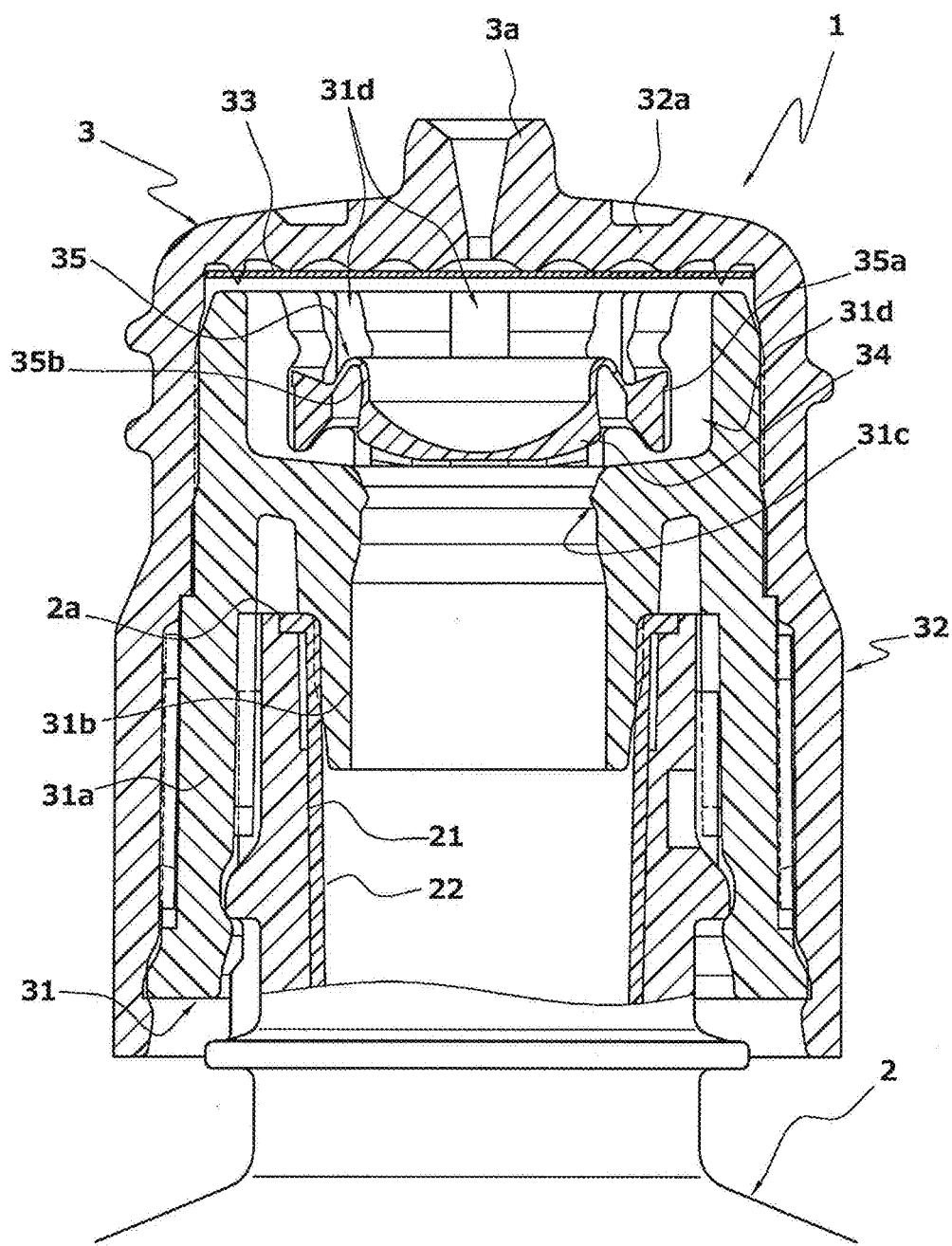
FIG. 5 is a sectional view showing the major portion of the container in an unsealed state.
Figure 6:
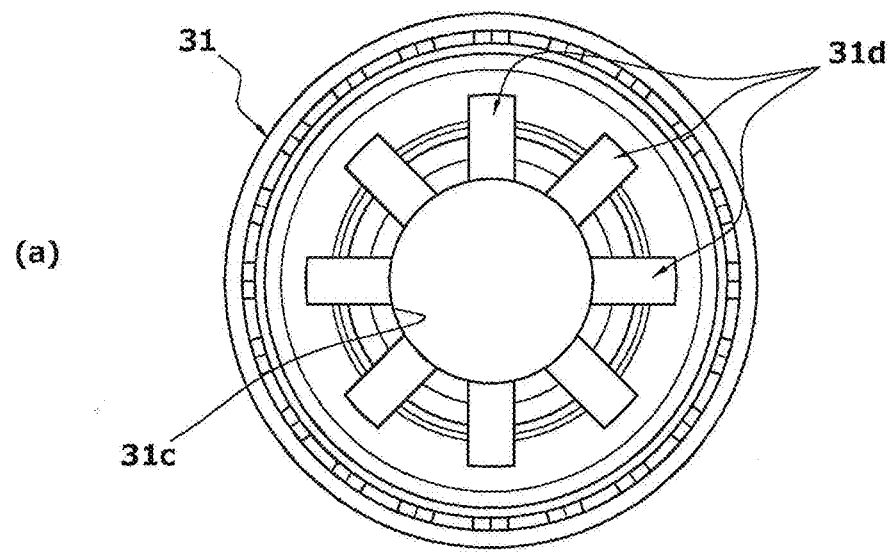
FIGS. 6(a) and 6(b) are a plan view and a vertical sectional view, respectively, showing a plug holder of the container.
Figure 6:
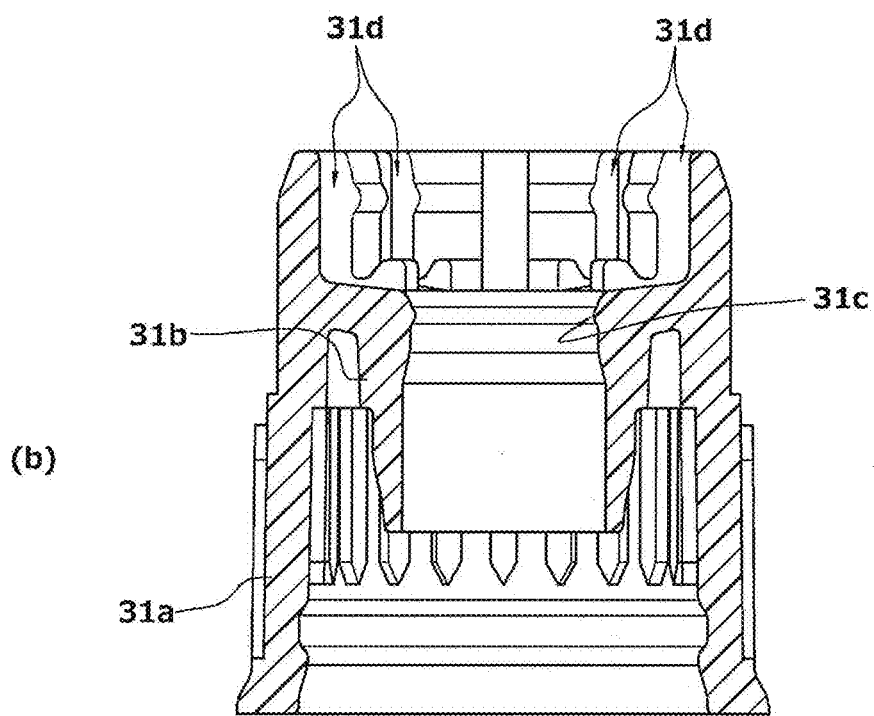

FIGS. 4 to 6 illustrate a filtering discharge container 1 according to a second embodiment of the present invention. Components corresponding to those in the first embodiment are designated by the same reference characters as in the first embodiment, and will not be described in detail. Therefore, different components and different functions and effects will be described.

In this embodiment, the plug 34 is formed from an elastic material such as a silicone rubber, a chlorinated butyl rubber or an elastomer. A plug flange 35a (base portion) and a connector sleeve 35b (resilient connection portion) constituting the resilient support member 35, and a plug head 34 constituting the plug 34 are integrally molded. The plug flange 35a has a generally ring shape, and has a triangular section having a thickness increased toward radially outward. The connector sleeve 35b has a generally hollow cylindrical shape. The connector sleeve 35b is integrally connected at one of axially opposite ends thereof to an inner peripheral edge of the plug flange 35a, and integrally connected at the other axial end thereof to the outer peripheral edge of the plug head 34. The connector sleeve 35b has a relatively thin and flexible structure for easy deformation and, as shown in FIG. 4, has a restoration resilience with respect to an axially shrinking direction when being axially elongated. The initial shape of the connector sleeve 35b is shown in FIG. 5. Of course, the plug head 34 is not formed with the cross-shaped orifice disclosed in PLT2.

Further, an upper end portion of a content liquid outlet portion 31b of a valve holder 31 has an inner surface having a diameter progressively reduced in an upward direction, and a minimum diameter portion of the content liquid outlet portion 31b defines an engagement hole 31c (engagement portion). The plug head 34 is liquid-tightly fitted in the engagement hole 31c from above. As shown in FIG. 6, at least one or more communication channels 31d are provided in circumferential positions on an inner peripheral surface of the valve holder 31 above the engagement hole 31c, so that the content medicinal liquid can flow out from outer peripheries of the plug head and the plug flange toward the filter 33 with the plug head 34 being located upwardly apart from the engagement hole 31c. In FIG. 6, eight communication channels 31d are circumferentially equidistantly arranged, so that the content medicinal liquid can uniformly flow out from the entire circumference of the plug head 34. The communication channels 31d each have an L-shaped vertical section.

In this embodiment, lower inner surface portions of side walls of the L-shaped communication channels 31d are configured so as to be engaged with or lock the plug head 34 pushed up by the content liquid in order to more reliably support the plug head 34 apart from the engagement hole 31c. With this arrangement, the plug head 34 is reliably supported in a position upwardly apart from the engagement hole 31c. Of course, the plug head 34 may be supported in the position upwardly apart from the engagement hole 31c only by the resilient restoration force of the connector sleeve 35b.

In the container 1 according to this embodiment, as shown in FIG. 4, the plug head (plug) 34 is engaged with the engagement portion 31c to reliably prevent the content medicinal liquid from leaking before the first discharging operation. In the second and subsequent discharging operation, as shown in FIG. 5, the plug head 34 is supported in the disengaged position, whereby the content liquid can be discharged with a smaller squeeze force.

The present invention is not limited to the aforementioned embodiments, but design modifications may be made as required. For example, the plug may be a spherical member without the provision of the base portion and the resilient connection portion. The present invention is applicable to a variety of dispenser containers and discharge containers other than the eyedropper container. The filtering discharge container according to the present invention may be applied to a two-component mixing container. In this case, for example, a first agent such as a less soluble powdery drug is contained in a space between the plug and the filter, and a second agent such as a solvent is contained in the inner layer bag of the laminate bottle. Before use, the plug is disengaged from the engagement portion to mix the first agent and the second agent together. Thus, the discharge container can be used for discharging a mixture liquid.

REFERENCE SIGNS LIST

1 FILTERING DISCHARGE CONTAINER
2 LAMINATE BOTTLE
21 OUTER LAYER BOTTLE
22 INNER LAYER BAG
3 MOUTH CAP
3a OUTLET NOZZLE

3*b* SUPPORT PORTION
31 PLUG HOLDER
31*c* ENGAGEMENT PORTION
32 COVER
33 FILTER
34 PLUG
35 RESILIENT SUPPORT MEMBER

The invention claimed is:

1. A filtering discharge container comprising:
an outer layer bottle including a squeeze-deformable body and a mouth portion provided at an upper end of the body;
an inner layer bag provided in the outer layer bottle and having an opening connected to the mouth portion of the outer layer bottle; and
a mouth cap attached to the mouth portion of the outer layer bottle;
the outer layer bottle having an inlet hole through which outer air is introduced between the outer layer bottle and the inner layer bag;
the mouth cap having an outlet passage through which a content liquid contained in the inner layer bag is discharged from the inner layer bag;
the outlet passage being provided with a filter;
the filtering discharge container further comprising:
an engagement portion provided on an upstream side of the filter in the outlet passage of the mouth cap;
a plug engaged with the engagement portion in such a manner that the plug can be disengaged from the engagement portion by an internal pressure of the inner layer bag increased by squeeze-deforming the body of the outer layer bottle; and
a resilient support member which urges the plug away from the engagement portion;
wherein the outlet passage is closed with the plug engaged with the engagement portion and, after the plug is disengaged from the engagement portion, liquid communication is established between an inside of the inner layer bag and the filter.

2. The filtering discharge container according to =claim 1, wherein the resilient support member supports the disengaged plug in a disengaged position.

3. The filtering discharge container according to claim 1, wherein the mouth cap includes:
a plug holder having the engagement portion which is provided in an upwardly open state so as to be combined with the plug from above;
a cover having a top portion;
the filter which is provided on a lower side of the top portion of the cover; and
the plug;
wherein the cover is fitted around the plug holder combined with the plug from above.

\* \* \* \* \*